(12) United States Patent
Rigoli (10) Patent No.: US 6,352,266 B1
(45) Date of Patent: Mar. 5, 2002

(54) SEAL FOR A LIQUID CHROMATOGRAPHY COLUMN

(76) Inventor: Michael J. Rigoli, 55 Metacomet St., Wrentham, MA (US) 02093

( * ) Notice: Subject to any disclaimer, the term of this patent is extended or adjusted under 35 U.S.C. 154(b) by 0 days.

(21) Appl. No.: 09/177,310

(22) Filed: Oct. 22, 1998

(51) Int. Cl.⁷ .............................................. B65D 41/20
(52) U.S. Cl. .................... 277/628; 277/918; 210/198.2; 210/353
(58) Field of Search ................................ 297/628, 634, 297/637, 917, 918, 636; 210/198.2, 353

(56) References Cited

U.S. PATENT DOCUMENTS

| | | | | |
|---|---|---|---|---|
| 4,084,718 A | * | 4/1978 | Wadsworth | 210/198.2 |
| 5,193,703 A | * | 3/1993 | Staats, III et al. | 220/203 |
| 5,286,407 A | * | 2/1994 | Inoue et al. | 252/188.28 |
| 5,609,757 A | * | 3/1997 | Schiavo et al. | 210/232 |
| 5,667,676 A | * | 9/1997 | Alaska | 210/198.2 |
| 5,833,860 A | * | 11/1998 | Kopaciewicz et al. | 210/650 |

* cited by examiner

*Primary Examiner*—Anthony Knight
*Assistant Examiner*—Mark Williams
(74) *Attorney, Agent, or Firm*—Lambert & Associates; Gary E. Lambert (57) ABSTRACT

A liquid chromatography seal capable of withstanding pressures in excess of 8000 to 10,000 psi utilizing an annular ring disposed upon either the seal or the seal seating surface. The annular ring is triangular in cross section. The triangular cross section forms three seals. The first seal is the innermost face of the triangular cross section, the third is the outermost face, and the second is the angle between the first and third. The structure of the seal enables the column to be leak-free even with a minimum of torque applied to the fasteners. Another important aspect of the seal is that it eliminates the need for a disperser frit since the seal itself acts as to disperse liquid to the frit.

14 Claims, 8 Drawing Sheets

SEAL FOR A LIQUID CHROMATOGRAPHY COLUMN

BACKGROUND OF THE INVENTION

1. Field of the Invention

The present invention relates to a seal for a liquid chromatography column.

2. Related Art and Prior Art Statement

A liquid chromatography column comprises a plurality of carefully sized particulate through which a liquid is filtered. The particulate, often times silica, is formed into a filter bed and retained within a column which is capped at each end with a porous device known as a frit or more specifically as a filter bed frit. The filter bed frits are held in place by column end fittings or caps which appropriately mount to each column end. Liquid is forced, usually through tubing, at high pressure into one column end fitting, through a filter bed frit, through the filter bed, out the second filter bed frit, and finally exiting out the second column end fitting. A sealing means, commonly an o-ring or gasket is used to seal each column end fitting to the column. To allow for a more uniform dispersal of the liquid, some mechanism is typically provided between the filter bed frit and the column end fitting which is designed to divert the liquid over the entire filter bed frit. One manner of accomplishing this dispersal is to machine grooves into the column end fitting at the surface facing the filter bed frit. These grooves are intended to provide a path for distribution of the liquid over the entire surface area of the filter bed frit. Another option is to use a disperser. The disperser, essentially another frit, spreads the liquid evenly across the filter bed frit by providing a number of pores arranged in a pattern over the entire surface area of the disperser frit. These pores are designed to allow the liquid to pass with minimal interference. A combination of the disperser frit and grooved end fittings are also utilized. Frequently when a disperser frit is used, the column is sealed with double o-rings at each end. The first or interior o-ring is designed to stop the majority of the leakage and the second o-ring stops whatever liquid may have escaped the first.

The field of liquid chromatography can be subdivided into two major classifications or categories. The first utilizes a preparatory column and the second, an analytical column. Preparatory columns are used for processing large amounts of liquid by quickly stripping the incoming liquid stream of some of its constituent chemical components. The outcoming liquid stream is further separated by preparatory columns until a relatively pure liquid results. Once a satisfactory purity has been reached with the liquid stream, the stream is placed into an analytical column. The analytical column works identically to the preparatory column but processes a much smaller quantity of liquid. Where the preparatory column acts as a bulk separator, the analytical column separates specific components out of the stream resulting in a very high degree of purity. However, oftentimes to create large quantities the reverse is true as well. An analytical column is first used to establish the constituents of the filter bed best suited to extract a particular liquid stream. Once the bed is identified it is scaled upwards and used in a preparative column in order to perform bulk separation to more rapidly process the liquid stream and obtain larger quantities of the desired end product.

As important as these chromatography columns are to many emerging scientific and technical fields, the current design is subject to numerous problems and deficiencies. One major problem associated with chromatography columns pertains to the use of o-rings. The use of o-rings forms a limitation to the column's operating pressure which is approximately 3000–4000 psi. Typically o-rings are manufactured from neoprene which is not resistant to the chemicals these units often see. To increase their chemical resistivity, the o-ring is often encased in teflon. The teflon, however, does not possess the same elastic qualities that make neoprene a desirable o-ring. O-rings manufactured in this manner simply do not function sufficiently well to enable the use of higher pressures and thus higher outputs. Not only do the o-rings need to function properly but in order for the column to remain sealed at these pressures, proper alignment must exist between each of the internal components, that is, the filter bed frit, the disperser frit, and the interior and exterior o-rings if a double o-ring system is used.

The problem associated with sealing the columns becomes even more troublesome since the processing of the liquid oftentimes requires that the column be continuously replaced during use. The technician still must replace the column when it is desirable to separate different components from the stream or when the column is spent. This process though not technically a difficult job, requires proper tooling, some care, and a significant quantity of time to assemble the column correctly to ensure that the column does not leak under high pressure. An analytical column though often disposed of when spent, often times utilizes a threaded fitting and requires the use of wrenches to install and remove. Frequent replacement requires a significant expenditure of time on the part of the technician better utilized elsewhere.

Preparative columns, on the other hand, are often reused. These columns are frequently provided with threaded fasteners to secure the end fitting to the column. In order to maintain a leak-free operating status, these fasteners are torqued to a significant load. As the filter bed is replaced and the column reused, the fasteners are subjected to a recurring cyclical load as they are first torqued and subsequently removed over and over again. This cyclical loading increases the likelihood of failure due to fatigue. Another problem, associated more often with double o-ring systems, is that it has been found that liquid leaks between the two o-rings forming a dead volume which reduces the effectiveness of the column, wastes a portion of the liquid sample and could even be hazardous as this dead volume of liquid is spilled when the column is removed from the system.

What is needed is a liquid chromatography column capable of quick replacement and substitution. The desired column would exhibit features enabling it to be simple to replace, easy to obtain a proper seal capable of withstanding 8000–10,000 psi pressures which will result in increased column throughput and sample processing time, while eliminating a number of internal components and eliminating the potential for a dead liquid volume.

SUMMARY OF THE INVENTION

In view of the above, it is an object of the invention to provide a liquid chromatography seal which is simple in structure, low in cost, wherein seal leakage and failure is low, which is self-seating and seals without excessive force creating a leak-proof seal capable of withstanding pressures in excess of 8000 psi.

It is another object of the present invention to provide a chemically resistant seal without the disadvantages inherent to o-ring type seals.

Yet another object of the present invention is to provide a seal which increases the longevity of the column by reducing the forces associated with cyclical torquing of the fasteners.

Still another object of the present invention is to provide a single seal structure which serves to seal the column and disperse the liquid to the frit.

According to the invention, there is provided a liquid chromatography seal which in lieu of o-rings utilizes a series of sealing surfaces each disposed upon a single seal device. The physical construct of the seal device is dependent upon whether it is used in a flanged column or a threaded fitting type column. The first type is associated with preparative columns and the latter is associated with analytical type columns. The common element between the different configurations is the use of an angled seal. The angled seal, comprises an annular ring which in cross-section forms three separate contiguous sealing surfaces which in combination effectively seal the column against any leakage. Furthermore the seat upon which the seal is configured to rest is shaped to receive the seal in mated relation. To ensure a leak-proof seal, it is desirable for the chromatography seal to exhibit some characteristics of plastic deformation.

As the end cap is secured to the column, the seal is forced into its seat thus minimizing the chances for liquid to escape through the seal. Further, since alignment of the internal components goes a long way towards establishing a proper seal, the seal itself effectively serves to disperse the liquid over the surface of the filter frit. The seal replaces the o-ring in a preparative column and since no disperser geometry is necessary, it eliminates the disperser frit as well as the double o-ring seal. This reduction in parts not only resolves some of the sealing problems associated with current designs but also simplifies the device as well. When the seal is constructed in this fashion, elimination of dead volume and enabling the column to withstand pressures in excess of 8000 to 10,000 psi with a very low torque load are the results.

BRIEF DESCRIPTION OF THE DRAWINGS

The novel features considered characteristic of the invention are set forth in the appended claims. The invention itself, however, both as to its construction and its method of operation, together with additional objects and advantages thereof, will best be understood from the following description of the specific embodiments when read and understood in connection with the accompanying drawings.

DETAILED DESCRIPTION OF THE PREFERRED EMBODIMENTS

The First Preferred Embodiment

Figure 1:
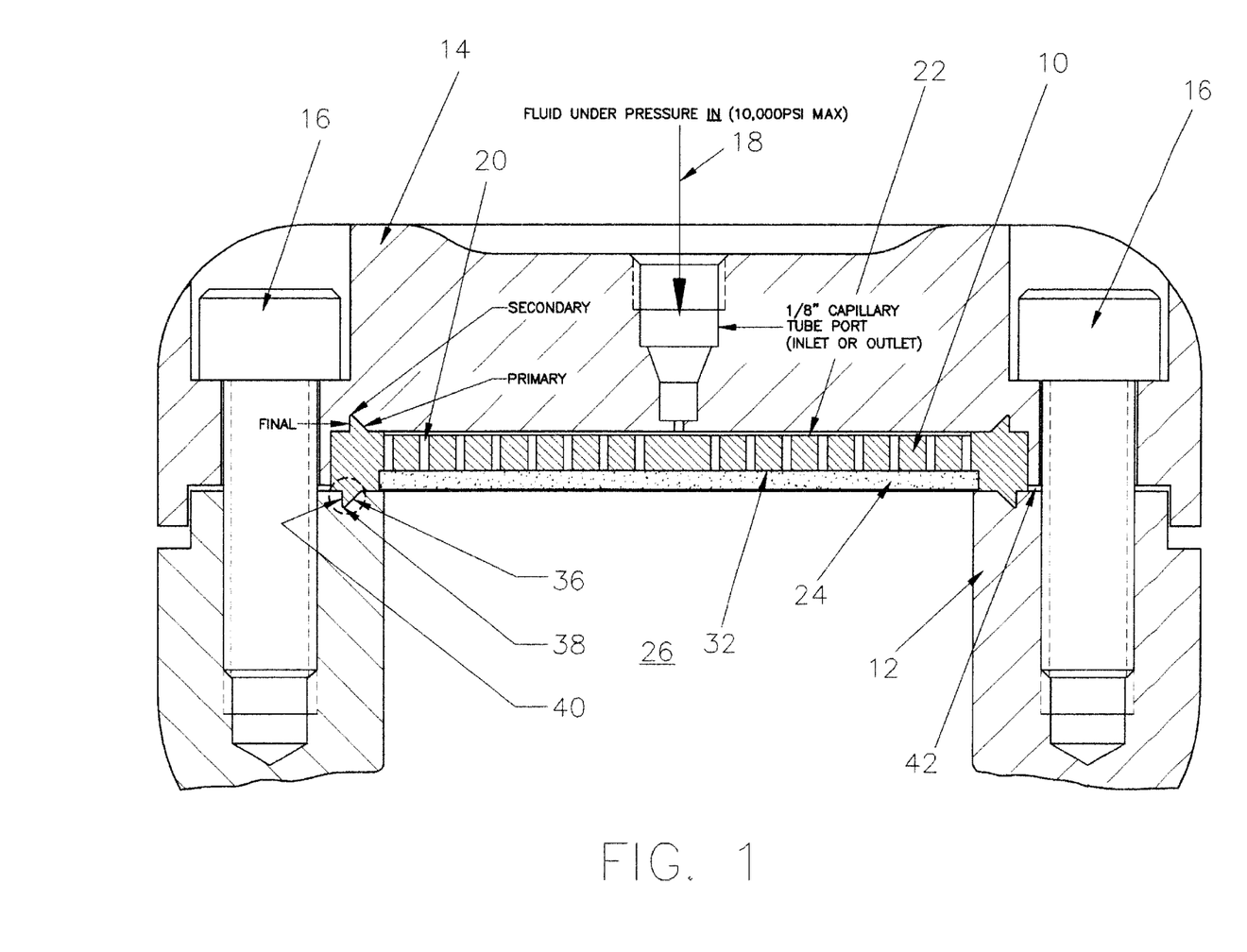
FIG. 1 depicts a cross section of a liquid chromatography column containing a seal in accordance with the first preferred embodiment of the present invention.

In accordance with FIG. 1, a preferred embodiment of a chromatography seal 10 is provided. The seal 10 is depicted in its intended environment which is within a chromatography column 12. The material of seal 10 should comprise a material capable of elastic or slight plastic deformation to ensure an adequate seal and be chemically non-reactive with the filtered liquid. Preferred materials are plastics or polymers. Some polymer materials which have proven useful in the device are polyetheretherketone (PEEK), chlorotrifluorethylene (PCTFE) known under the trademark Kel-F, polyphenylene sulfide known under the trademark Techtron, polyetherimide known under the trademark Ultem, polyvinylidene fluoride (PVDF) known under the trademark Kynar, and nylon. Though these polymers are well suited for most applications those skilled in the art will recognize adequate substitutions. Nevertheless, the column 12 is capped by an end cap 14 held into place by a plurality of end cap bolts 16 or other fastening devices. Chromatography columns of the type depicted and described are typically associated with the preparatory processing of liquids, hence they are known as preparatory columns. Liquid is piped under pressure into the column through one end cap 14. It is allowed to exit the column at the opposite end of the column through a similarly constructed end cap. Access through the end caps are had through a port 18 which is commonly located at the central axis of the column.

Figure 2:
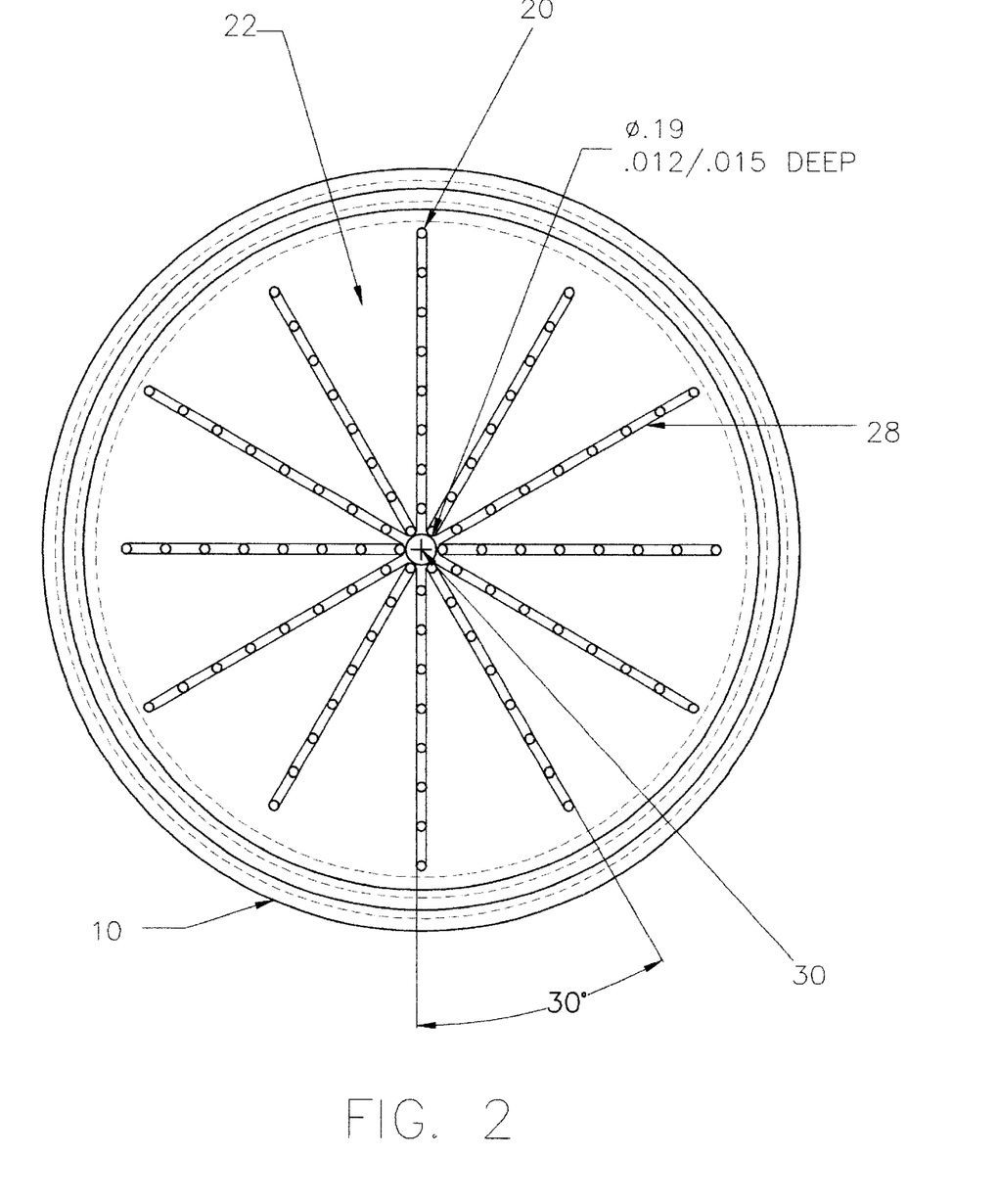
FIG. 2 depicts a plan view of that surface of the FIG. 1 seal intended to seat against a column end cap.

As liquid enters the port 18, it impinges upon the upper surface of the seal 10. Now looking at FIG. 2 in conjunction with FIG. 1 it can be seen that the seal 10 comprises a circular disk having a plurality of holes or pores 20 bored through the thickness of the seal 10. The surface depicted in FIG. 2 is oriented within the apparatus such that a first surface or an end cap contacting surface 22 rests against the interior face of the column end fitting or end cap 14. Liquid is allowed to proceed through the pores 20 and onto a first surface of a frit 24. The liquid continues through the porous structure of the frit 24 and enters the filter bed 26 where the filtration process occurs which is well known in the art and therefore not described.

To aid in the dispersal of liquid, careful examination of FIG. 1 will cause one to note that the pores 20 are arranged in a geometric pattern. The specific pattern itself is unimportant so long as it promotes an even distribution of liquid onto the surface of the seal. Since the seal 10 is seated tightly against the interior face of the column end cap 14; to aid in the dispersal of the liquid, surface 22 has a plurality of deepened grooves 28 interconnecting certain sequences of pores 20. This allows for passage of the liquid over the upper surface of the seal. The liquid typically enters the column at its central axis, thus one orientation of the pores 20 which best distributes the liquid has been found to be a radial pattern originating from the column's central axis. This allows for a central hub and spoke type arrangement of the interconnecting grooves 28. The central hub 30, or that point where the liquid exits port 18 and impinges upon the center of the seal 10, can also be slightly relieved so that it is at a depth as measured from surface 22 equivalent to the depth of the grooves 28. The actual depth for the grooves and the hub is preferred to be approximately 0.012 to 0.015 inch deep. However, it is envisioned that adequate liquid distribution will occur between the ranges of 0.005 and 0.030 inch deep. Making the grooves too shallow results in little to no flow whereas too deep could create a problem similar to the one encountered due to the dead volume discussed above. It should be understood that the use of the seal to perform the dispersal function simply replaces the need for some other form of disperser geometry. Therefore the pattern of holes, the pattern and depth of grooves and the depth of the central hub are mentioned only to provide a description of the best mode known at present. Other possibilities abound and would be readily substitutable and identifiable to those with ordinary skill in the art based upon the application.

Figure 3:
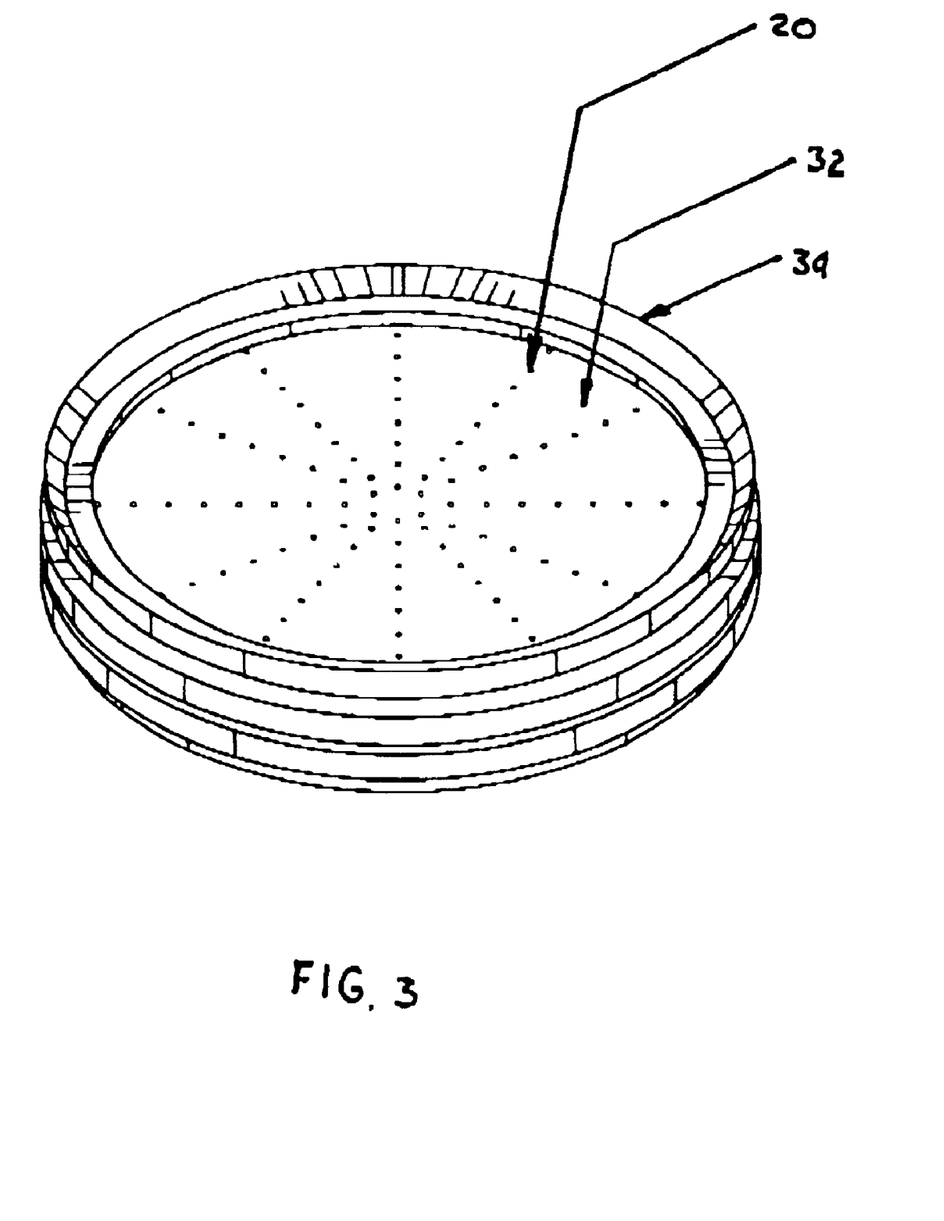
FIG. 3 depicts a perspective view of that surface of the FIG. 1 seal intended to seat against a frit.
Figure 4:
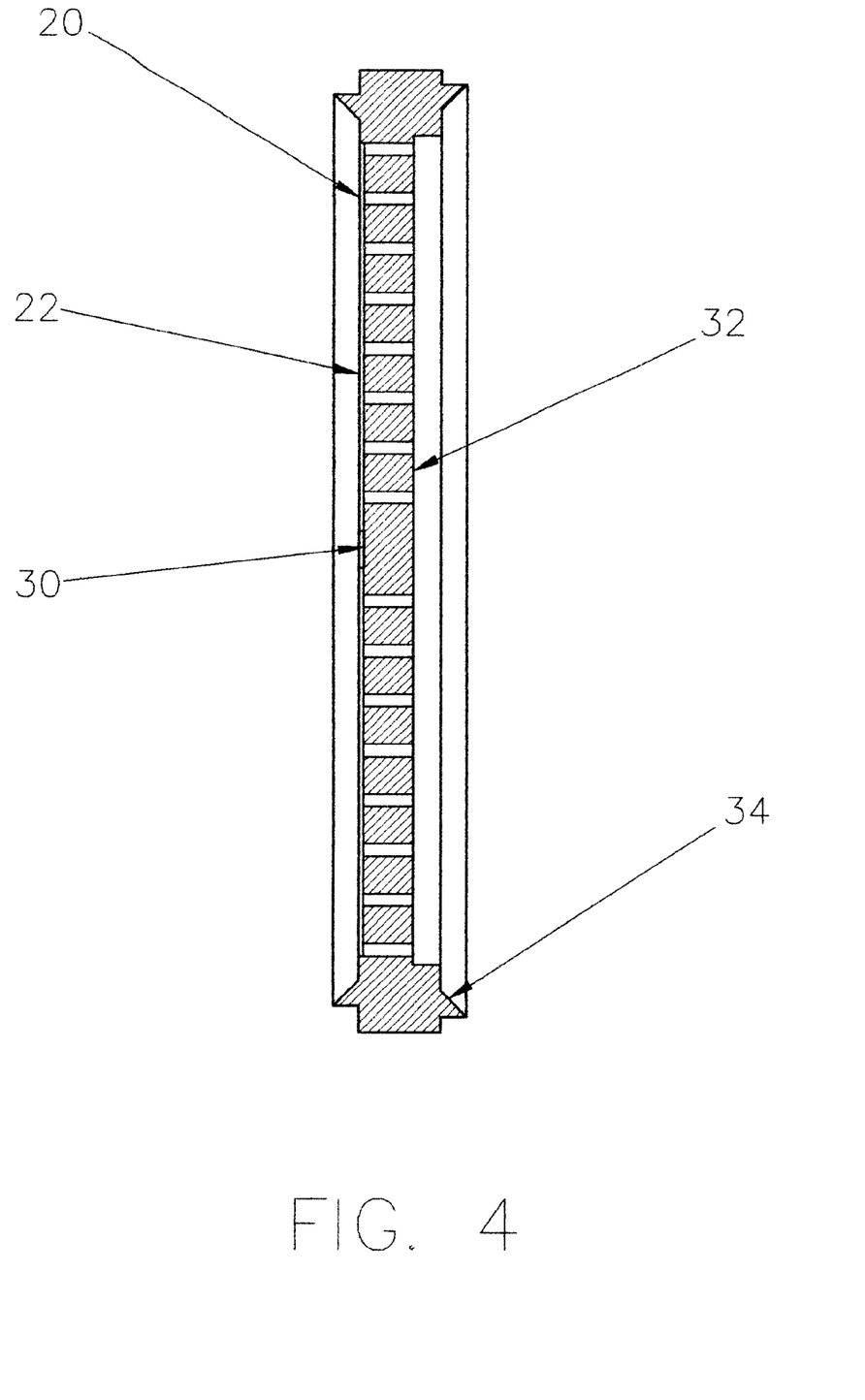
FIG. 4 is a cross section of the FIG. 1 seal.

Now looking at FIGS. 3 and 4, it is shown that the surface of the seal opposite the end cap contacting surface 22 is relieved. This surface, a frit receiving surface 32, is relieved sufficiently to centrally locate and maintain the position of the frit 24 within the apparatus. The diameter of the relief is such that the frit 24 fits snugly within. It has been found that by eliminating a separate dispersing element and housing the frit, a better liquid chromatography seal is created. One possible reason is that no binding or misalignment occurs between the components as is possible with the separate components found in an o-ring apparatus. This arrangement also eliminates any voids between the end cap 14 and seal surface 22 and the frit 24 and seal surface 32. With no voids, no possibility exists for liquid dead volume. As a result, the apparatus functions more safely and efficiently.

The most important aspect of the invention, which has no equivalent in the prior art, is the means for sealing the column against liquid leakage. The discussion above describes preferable limitations to such a seal element and as such makes a more efficient product. The gist of the invention, however, is the means used to seal the column from leakage. The means to seal the column comprises three pressure surfaces or seals; a primary, a secondary, and a tertiary or final surface. These pressure seals are shown enlarged in FIG. 5 for clarity. The three pressure surfaces are formed by a single annular ring 34 which protrudes from either surface 22 or 32 of the seal 10. In the preferred embodiment an annular ring 34 protrudes from each surface 22 and surface 32. The center of each ring is concentric about the centerline of the seal and each surface 22 and 32 are planar. Taking a cross-section through any portion of either ring reveals that the ring comprises a triangular raised surface with a first seal surface 36, a second a tertiary seal surface 40, and a second seal surface 38 formed between the first and tertiary faces. The tertiary face 40 is perpendicular to the surface 22 and 32 of the seal, whereas the first face 36 is angled with respect to the surfaces 22 and 32. An angular dimension of 45 degrees plus or minus one-half degree has been found to provide excellent results for angle 38 and should easily be achievable. However, it is envisioned that sealing will occur between the ranges of 15 degrees to 80 degrees, the closer to 45 degrees nominal the better the seal. By dimensioning the face 40 to 0.0625 inch, simple trigonometry will provide the length of face 36. Accuracy to this degree serves only to provide guidelines for the best mode known to the inventor to assist one skilled in the art. It must be emphasized that the angle formed between the first seal surface 36 and the tertiary seal surface 40 and dimensions of faces 36 and 40 which have been disclosed above comprise the best measurements known. A more simplified explanation of what range is considered to comprise the patentable invention without resort to dimensions is that the face 36 should be greater in length than the length of face 40. This description is believed to provide an appropriate degree of latitude in the design of the three pressure surfaces to sufficiently disclose the invention.

Once again referring to FIG. 1 it can be seen that regardless of the cross-sectional dimensions of the annular ring 34, the end cap 14 is recessed to intimately receive said seal 10 therein. A majority of the seal is therefore seated within said end cap 14. The surface 32 which comes in contact with the frit 24, including the annular ring 34, protrudes from the end cap 14. To ensure adequate sealing of the column assembly, when the seal 10, and the frit 24 are inserted within the end cap 14, and this entire assembly is placed upon the column 12, a gap 42 separates the column 12 and the end cap 14. By tightening the bolts 16, the gap 42 is reduced by compressing the seal 10.

Figure 5:
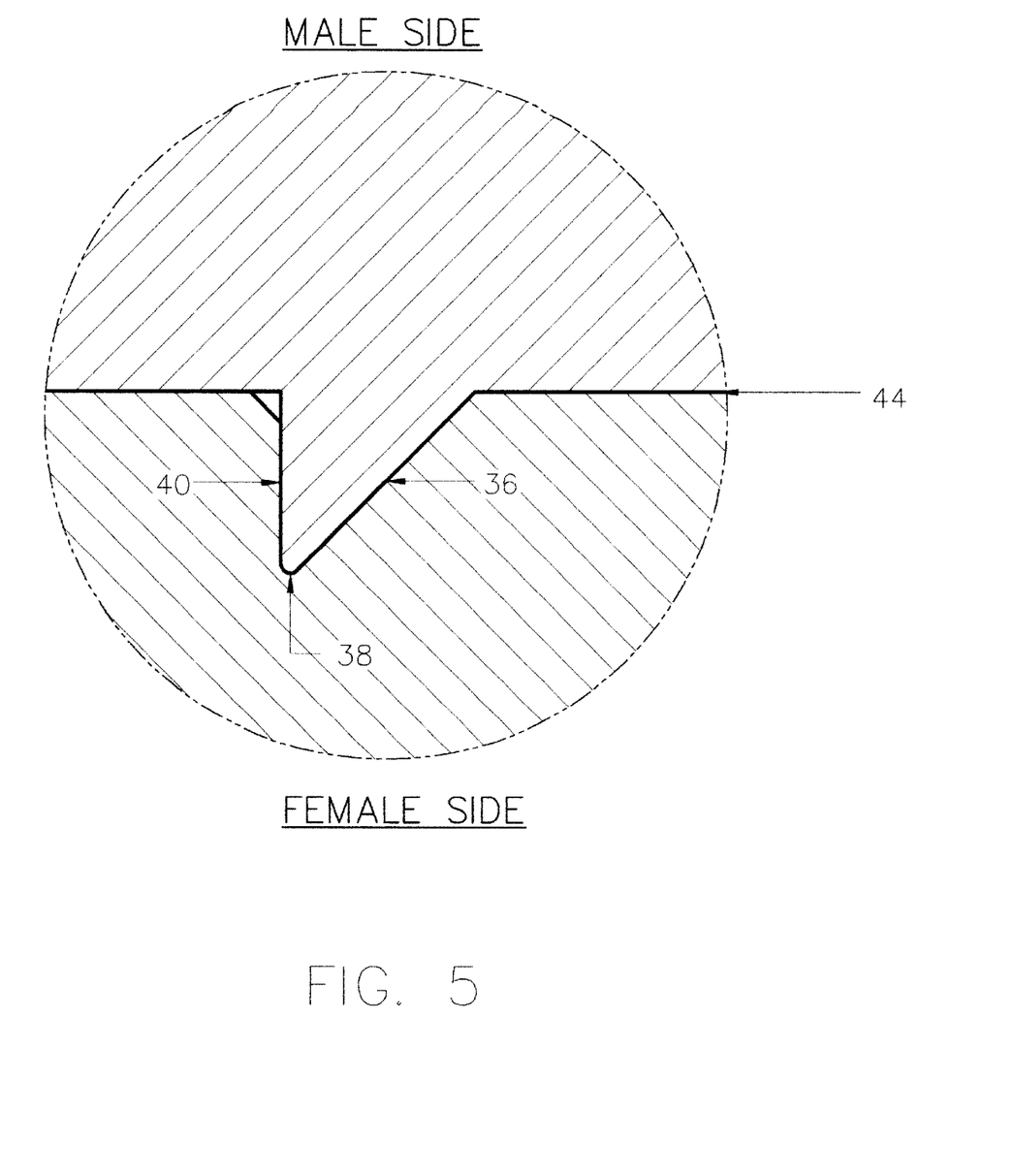
FIG. 5 is an enlarged cross sectional view through the seal.

Once the bolts are tightened sufficiently and liquid is forced into the column apparatus under high pressure through port 18, as illustrated in FIG. 5, any liquid attempting to escape the column apparatus is forced between the interface 44 of the column 12 and the seal 10. The liquid enters the pathway depicted as the interface 44 and progresses outward until it encounters the primary surface at face 36. Any liquid successfully progressing past the primary surface encounters the secondary surface at angle 38. Though little liquid should make it to the secondary surface, even less has been found to progress to the tertiary surface at face 40. An important aspect regarding the shape of the annular ring is that as the inlet pressure at port 18 is increased, the pressure also increases on the primary surface at face 36 which in turn causes the tertiary surface at face 40 to seat even tighter thereby decreasing the likelihood of liquid escaping the column apparatus.

It should be understood that, according to this invention, sealing is not directly correlated to the torque placed upon the bolts 16 which hold the end cap 14 to the column 12. Sealing is a function of the matching interface between the seal 10 and each of the column 12 and the end cap 14. In summary the three pressure surfaces form the minimum elements of the invention. However, as discussed above, the best method of making and using the presently described embodiment contains; 1) the recessed circumferential area for seating and retaining the filter bed frit 24; and 2) the pores 20 through the seal and grooves 28 to allow proper dispersion of the liquid through the seal.

The Second Preferred Embodiment

Figure 6:
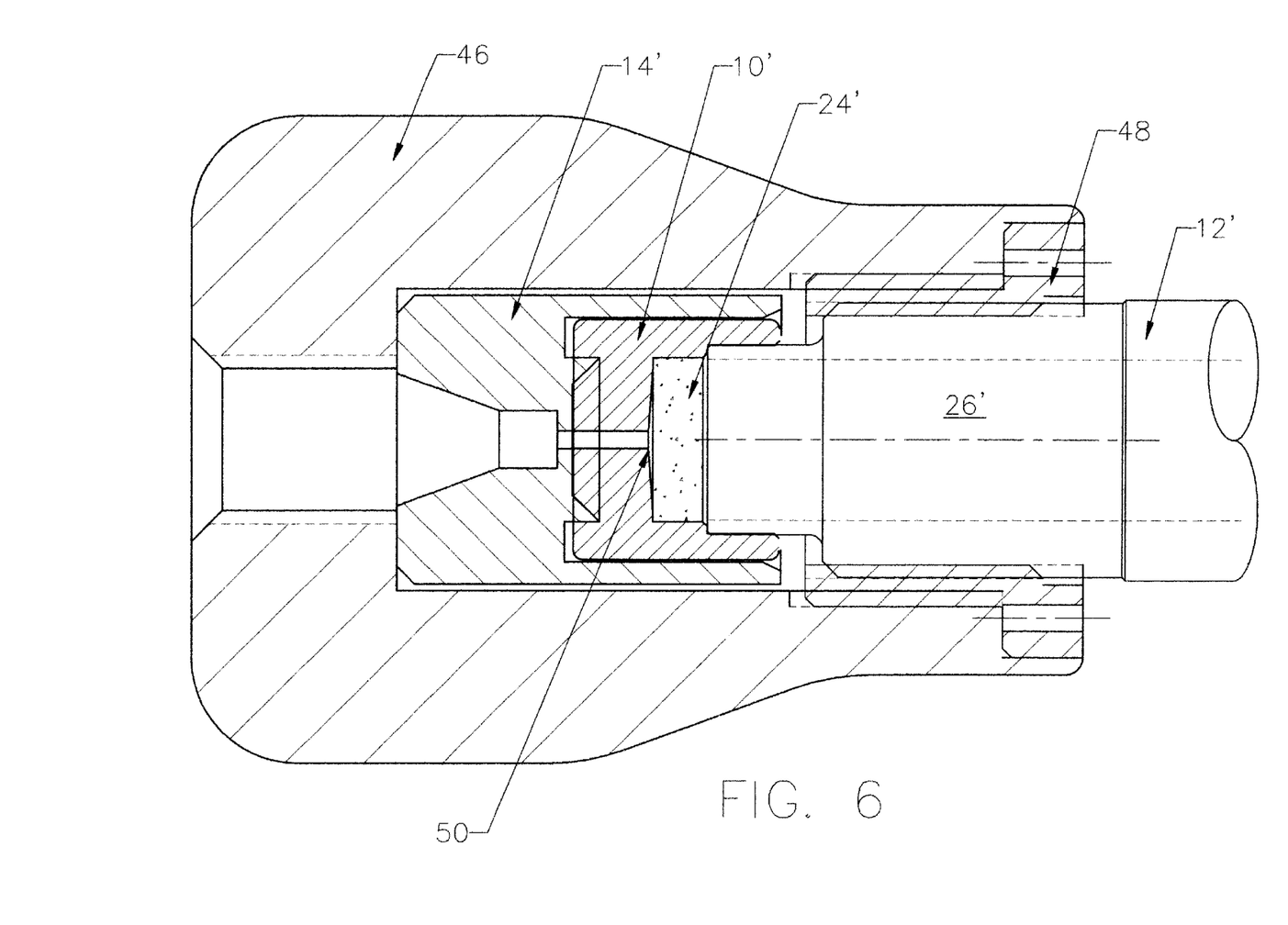
FIG. 6 depicts a cross section of a liquid chromatography column containing a seal in accordance with the second preferred embodiment of the present invention.
Figure 7:
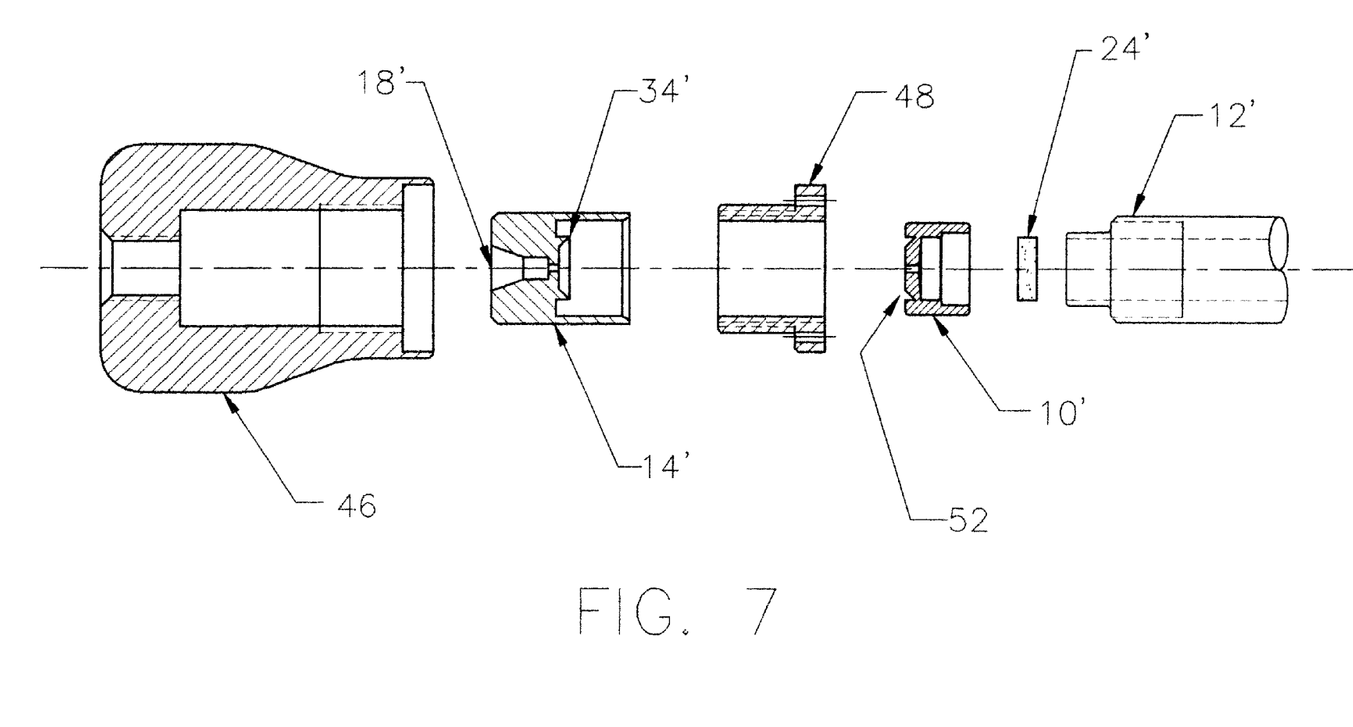
FIG. 7 depicts an exploded view of the FIG. 6 liquid chromatography column to illustrate the relationship between the seal and the remaining components.

In accordance with FIGS. 6 and 7, an alternative preferred embodiment of a chromatography seal 10' is provided. The two seals 10 and 10' are structurally identical with respect to the three pressure seals, hence they are considered identical in terms of patentability. FIG. 6 depicts the seal 10' in its intended environment which is within an analytical type chromatography column 12'. A frit 24' is retained within the seal 10', and the resulting combination seats tightly and is retained upon an end of the column 12'. This feature enables the column 12' to be capped by the seal 10' thereby preventing the filter bed media 26' from emptying from the column in the event the column assembly is disassembled.

A frit cap seal 14' is loosely held within a housing 46. In this embodiment, the seal 10' is also made of the polymer and the frit cap seal 14' is made of a harder substance, preferably metal, and one which is non-reactive to the liquid. The column 12' with seal 10' is inserted into the housing 46 where the seal 10' seats upon the frit cap seal 14' very much like the First Embodiment. The frit cap seal 14' is allowed to float within the housing 46 to ensure that the frit cap seal and seal properly seat one with the other. A sleeve or insert 48 is provided to more accurately align the components concentrically as well as prevent galling of the column 12'.

Figure 8:
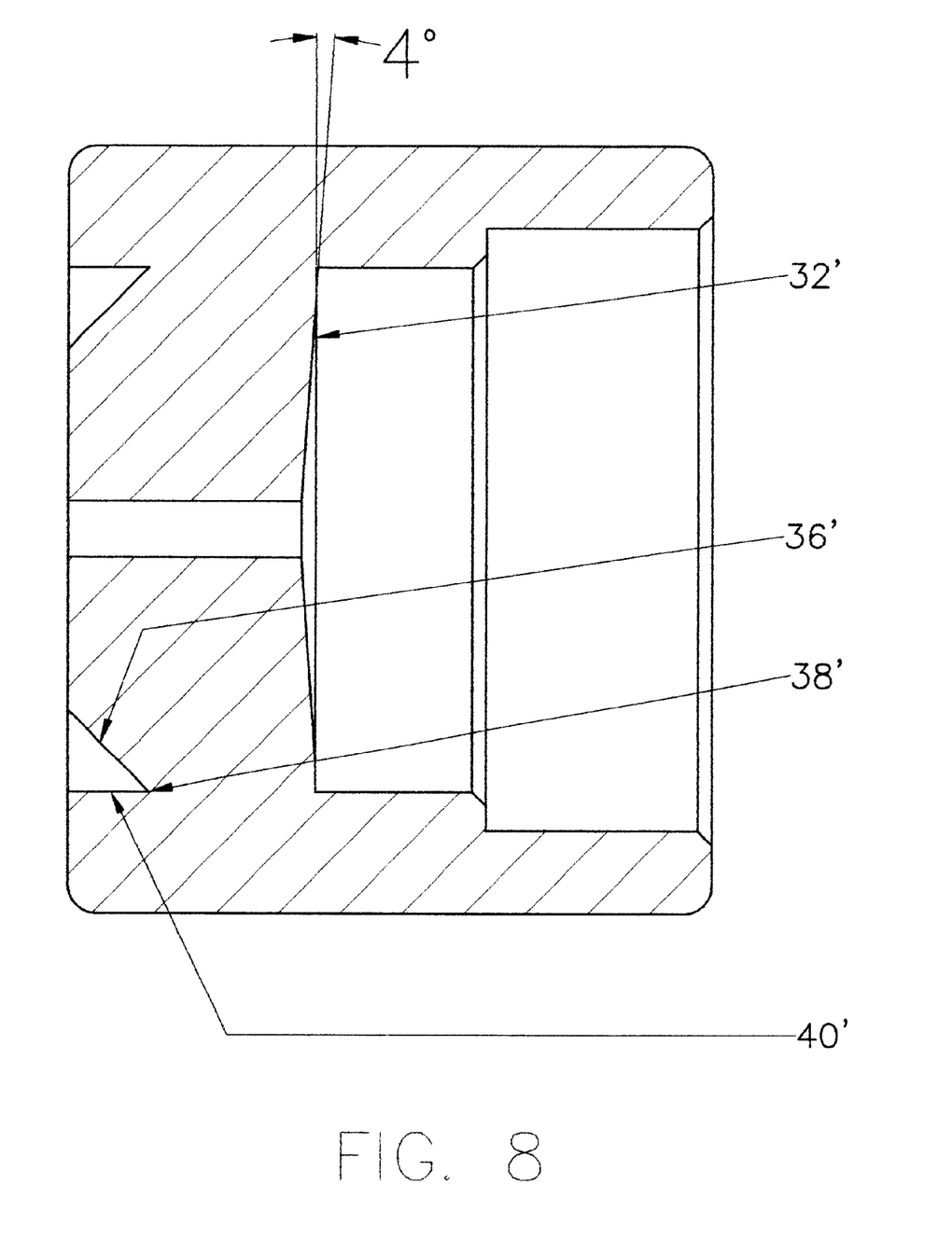
FIG. 8 depicts the seal of FIG. 6.

Liquid is piped under pressure into the column through one housing 46, one frit cap seal 14' via a port 18'. The filtered liquid is allowed to exit the column at the opposite end of the column through a similarly constructed housing and frit cap seal. Now looking at FIG. 8, it can be seen that an otherwise planar surface 32' which contacts the frit 24' is very slightly angled, in the preferred embodiment specifically, to 4 degrees. This angle creates a slight pocket between the surface of the frit 24' and the surface 32' within which fluid can collect. This pocket or void 50 is extremely small and is contained within the column and seal combination itself. Therefore not only will no liquid spill from the void 50 upon disassembly but the void does not constitute the dead volume referred to in the First Embodiment. The purpose of the void 50 is to allow the liquid access to the entire frit surface, similar to the disperser previously explained.

The seal 10' also comprises three similar pressure sealing faces, 36', 38' and 40'. These pressure faces operate identically to those of the First Embodiment and thus FIG. 5 should suffice as an adequate illustration. As is the case with the First Embodiment, the three pressure sealing faces are formed by a single annular ring 34. However, instead of protruding from the face of the seal 10', the annular ring 34' actually protrudes from the face of the frit cap seal 14'. As such, in order to effect sealing of the apparatus, the seal 10' therefore has a corresponding receiving annular groove 52 machined therein to receive said annular ring 34'. Though the angle is inverted from one embodiment to the other, the ring 34' and groove 52 are structurally identical to the same elements in the First Embodiment.

Due to the construction of the housing 46 and use of the insert 48, seating of the ring 34' into its receiving groove 52, is accomplished by hand tightening. No tools are required to maintain a leak proof seal even though 10,000 psi enters the port 18'. As liquid enters the port 18' and impinges upon the frit 24', any liquid attempting to escape the column apparatus is forced between the interface 44'. This liquid encounters the primary surface at face 36' and then the secondary surface at angle 38'. Similar to the First Embodiment, as the pressure increases on the primary surface at face 36', the tertiary surface at face 40' is forced to seat even tighter thereby decreasing the likelihood of liquid escaping the column apparatus.

As such the method of making and using the device detailed above constitute the preferred embodiments to the invention. It sis understood that numerous configurations of the device as a whole or some of its constituent parts are available which would provide the desired results. While the invention has been described and illustrated with reference to specific embodiments, it is understood that these other embodiments may be resorted to without departing from the invention. Therefore the form of the invention set out above should be considered illustrative and not as limiting the scope of the following claims.

What I claim as my invention and desire to secure by Letters Patent of the United States is:

1. A seal device for a liquid chromatography column comprising:
    a seal element having a first and a second substantially planar surface opposing one another;
    a seal element mating surface disposed upon the seal device and proximate to said seal element upon which the first surface of said seal element seats;
    a raised annular ring disposed upon the first surface of said seal element, said annular ring having a triangular cross-sectional profile defining a primary seal surface, a secondary seal surface and a tertiary seal surface, wherein the primary seal surface being located radially closest to the center of said seal element, the tertiary seal surface being located radially most distant to the center of said seal element, the primary seal surface and the tertiary seal surface forming two sides of the triangular cross-sectional profile and the secondary seal surface being located at the junction of the primary seal surface and the tertiary seal surface;
    a groove disposed upon the first surface of said seal element for intimately and matingly receiving said annular ring therein in fitted relationship; and
    a closure means located on the seal device for drawing the first surface of said seal element and the seal element mating surface of the seal device closer one to the other.

2. A seal device in accordance with claim 1 wherein the length of said primary seal surface is longer than the length of said tertiary seal surface.

3. A seal device in accordance with claim 1 wherein said primary seal and said tertiary seal surfaces forming two sides of the annular ring triangular cross-sectional profile forms an angle therebetween in a range from about 15 degrees to about 80 degrees.

4. A seal device in accordance with claim 1 further comprising:
    a column having a seal element mating surface upon which the second surface of said seal element seats;
    a second raised annular ring disposed upon the second surface of said seal element, said second annular ring having a triangular cross-sectional profile defining a primary seal surface, a secondary seal surface and a tertiary seal surface, wherein the primary seal surface being located radially closest to the center of said seal element or said column, the tertiary seal surface being located radially most distant to the center of said seal element or said column, the first seal surface and the tertiary seal surfaces forming two sides of the triangular cross-sectional profile and the secondary seal surface being located at the junction of the primary seal surface and the tertiary seal surface; and
    a groove disposed upon said second surface of said seal element for intimately and matingly receiving said annular therein in fitted relationship.

5. A seal device in accordance with claim 4 wherein said first and second annular rings are disposed upon the first and second surfaces of said seal element respectively and said grooves are disposed upon the seal element mating surface of the seal device and the seal element mating surface of the column for intimately and matingly receiving the second annular ring therein in fitted relationship respectively.

6. A seal device in accordance with claim 4 wherein the primary seal surfaces are longer than said tertiary seal surfaces.

7. A seal device in accordance with claim 4 wherein the primary and the tertiary seal surfaces forming two sides of the annular rings triangular cross-sectional profile forms an angle therebetween in a range from about 15 degrees to about 80 degrees.

8. A seal device in accordance with claim 6 wherein said seal element comprises a chemical resistant material softer than the seal mating surface of the seal device or the column.

9. A seal device in accordance with claim 8 wherein said seal element comprises a plastic.

10. A seal device in accordance with claim 1 wherein said annular ring is disposed upon the first surface of said seal element and said groove is disposed upon the seal element mating surface of the seal device.

11. A seal device in accordance with claim 10 wherein the length of the primary seal surface is longer than the length of the tertiary seal surface.

12. A seal device in accordance with claim 11 wherein the primary and the tertiary seal surfaces forming two sides of the annular ring triangular cross-sectional profile forms an angle therebetween in a range from about 15 degrees to about 80 degrees.

13. A seal device in accordance with claim 11 wherein said seal element comprises a chemical resistant material softer than the seal mating surface of the seal device.

14. A seal device in accordance with claim 13 wherein said seal element comprises a plastic.

* * * * *